United States Patent [19]

Heitman et al.

[11] 4,298,801
[45] Nov. 3, 1981

[54] L-U ARM HANDLE ASSEMBLY

[75] Inventors: Christopher J. Heitman; Gregory D. Schwehr, both of Milwaukee, Wis.

[73] Assignee: General Electric Company, Milwaukee, Wis.

[21] Appl. No.: 112,866

[22] Filed: Jan. 17, 1980

[51] Int. Cl.³ .............................................. A61B 6/04
[52] U.S. Cl. .................................. 250/447; 250/449; 250/521; 250/525
[58] Field of Search .................. 250/439 R, 446, 447, 250/521, 525, 448, 449

[56] References Cited

U.S. PATENT DOCUMENTS 3,609,355 9/1971 Schwarzer ......................... 250/448

FOREIGN PATENT DOCUMENTS

1099338 2/1961 Fed. Rep. of Germany ...... 250/521
1112808 8/1961 Fed. Rep. of Germany ...... 250/447

Primary Examiner—Alfred E. Smith
Assistant Examiner—T. N. Grigsby
Attorney, Agent, or Firm—Dana F. Bigelow; Douglas E. Stoner

[57] ABSTRACT

Movement control of an L/U arm combination of a medical diagnostic apparatus is maintained by the use of a single handle mounted on the patient table and provision is made for temporarily removing the handle for sterilization and for easily replacing the handle for subsequent use. The handle can be operated by a single hand of an operator to selectively rotate either or both of the L/U elements in either direction on their axes or to move the patient table, longitudinally or laterally, to a desired position. An enabling lever is also provided on the handle such that no movement of the components can occur until the enabling lever has been depressed as by the operators grasping the control handle.

29 Claims, 13 Drawing Figures

L-U ARM HANDLE ASSEMBLY

BACKGROUND OF INVENTION

This invention relates generally to control systems and, more particularly, to a single handle control for dual axis components of a angiographic apparatus.

Most present day diagnostic fluoroscopy systems consist of an x-ray tube, an image intensifier tube, an optical system, and a television camera and monitor or, alternatively, an optical viewer. The system can be arranged in any of a number of forms depending upon the particular application and equipment with which it is to be used. The common application is to classical angulating tables wherein the image intensifier system is usually mounted above the table on the spot film device. In some cases, if the intensifier, optics, and camera are of sufficiently light weight, no further supporting structure is necessary. In other cases, however, especially with the addition of film recording cameras, some means of auxiliary suspension is required, usually on a moving bridge supported from the ceiling. In any case, the x-ray tube position for such an angulating table arrangement is always under the table and in a fixed relationship with respect to the table.

In other systems, such as in remote control systems and in systems designed for urological procedures, the imageing intensifier is positioned under the x-ray table and the x-ray tube is positioned thereabove. Such an arrangement allows the selective positioning of the x-ray tube with respect to the patient, but, even though the table itself may be tiltable, the image intensifier tube can only be moved in one plane below the table.

Because of the limited flexibility of the systems described hereinabove, and because of the requirements in vascular procedures for oblique views which cannot be obtained by such arrangements, special fluoroscopic equipment arrangements have been developed for use in vascular procedure rooms. These rooms and the equipment used therein are specifically designed for cardio-vascular, viscerial, peripheral, neurological and angiographic procedures. In order to accommodate these oblique views at the various angles of choice, it has become common practice to use an island type of table, that is with no supporting structure for either the image intensifier or x-ray tube components. Support of these elements can be provided by a special ceiling mounted supporting structures with telescoping arms. Movement of these supporting members permits positioning of the image system for an anterior view, and also allows for 90° rotation. The x-ray tube for the anterior view is usually fixed within the base of the x-ray table, and for lateral views an auxiliary tube mounted on an overhead hanger is brought into place. In the interests of maintaining the patient in a fixed position, there is no table angulation in such a system.

In order to provide even greater flexibility with regard to position accessibility and choice of viewing angles, a "C" arm type of installation was developed wherein the image intensifier and x-ray tubes are connected to opposite ends of a semicircular arm which may be brought in around the patient for anterior, lateral, or any oblique views. A special adaptation of this C-arm installation was developed by the XRE Corporation wherein the C-arm was rotatably mounted on a horizontal axis from one leg of an L-arm whose other leg was parallel with the floor and rotatably supported on a vertical axis. This combination, commonly known as the L/U arm, is commonly located near an island-type table which is not tiltable but which is movable in the vertical and horizontal directions and is rotatable about its vertical axis.

Positional control for the L/U arm combination and for the associated patient table has normally been provided by an elongate control box mounted on one side of the table. Individual joysticks on the top of the control box serve to actuate the respective L and U-arm components, as well as the table locks, when manipulated by the operator. That is, there is one joystick which serves to operate the L-element and another joystick which serves for rotating the U-element, and since the joystocks were designed to be moved transversely, there is no logical directional correspondence between that transverse movement and the resulting rotational direction of the L or U-element.

Also forming part of the control box is a stainless steel handle extending horizontally from the box to simply provide a handle for manually moving the table in the longitudinal or lateral directions. Release of the locking mechanism within the table is accomplished by depressing a release trigger on the handle at the same time as the handle itself is being manipulated. Provision is made for removing the stainless steel handle for purposes of sterilization and for replacing it on the control box for subsequent use. The joysticks are not so removable and, in order to avoid contamination, it is desirable to cover them with a sterile sheet and to operate them through the sheet. Thus, in addition to the difficulty of associating the various movements of the joysticks with the desired movements of the L and U-elements, it is awkard to move both of the L and U-elements at the same time. Further, if it is desired to move the table at the same time, it would require the use of both hands and one foot of the operator, inasmuch as it would be necessary to operate the stainless steel handle with one hand, a joystick with the other hand, and the enabling mechanism, which is essentially a safety lock for the L and U elements, with his foot.

It is, therefore, an object of the present invention to provide an improved movement control system for an angiographic apparatus.

Yet another object of the present invention is the provision for efficiently and easily controlling the rotational positions of the individual L and U-elements of a angiographic L/U-arm combination.

Still another object of the present invention is the provision in a L/U-arm control for a single handle which operates both the L and the U-elements.

Another object of the present invention is the provision in an L/U-arm control system for operating both the L and U elements simultaneously.

Another object of the present invention is the provision in an L/U-arm control system for operating the L and U elements with only a single hand of an operator.

Still another object of the present invention is the provision in an L/U-arm control apparatus for a single handle which can be conveniently removed for sterilization purposes, and which can be operated by the single hand of an operator to simultaneously cause movement of the L-element, U-element and the table.

These objects and other features and advantages become more readily apparent upon reference to the following description when taken in conjunction with the appended drawings.

SUMMARY OF THE INVENTION

Briefly, in accordance with one aspect of the invention, a control box is provided with a plurality of switch pairs which control the circuitry for actuating the rotation of the L and U-elements, respectively, for releasing or engaging a lock mechanism for the movement of the table, and for electrically enabling the L and U-arm actuation means. Operation of the switches is accomplished by a single handle which extends through an aperture in the housing of the control assembly to provide various surfaces which may be selectively engaged with the contacts for the switches by appropriate operator movement of the handle. The rotation of the handle itself within the aperture of the housing causes a rotation of the U-element in a direction corresponding to the rotation of the handle. Means are further provided to bias the handle to the neutral position. Control of the L-element is provided by the manipulation of a lever rotatably mounted on the handle and, again, the rotation of the lever will cause a rotation of the L-element in either direction, but in a direction corresponding to that of the L-control lever. An operator can thus manipulate both the basic handle and the L-control lever with a single hand to simultaneously cause movement of the L and U elements.

By another aspect of the invention, the handle, as rotatably attached thereto, an enabling lever, which when depressed by an operator's grasping the handle, will enable the circuitry which allows the L and U-arm elements to be rotated. Also rotatably attached to the handle, in the vicinity of the enabling lever, is a panning lever which, when depressed, will unlock the table and allow the table to be manually "panned" in the longitudinal or horizontal direction. Both the enabling lever and the panning lever are in positions on the handle which would allow the single hand of an operator to operate them simultaneously with rotation of the basic handle and of the L-control lever.

By still another aspect of the invention, the control handle, together with the L-control lever, the enable lever, and the panning lever, may be removed by the releasing of a pin which is baised to lock the handle within the housing. When removed, the handle with its included levers, can be sterilized by an autoclave, or the like, and replaced within the housing aperture to reestablish control of the various switches by the use of a sterile handle.

In the drawings as hereinafter described, a preferred embodiment is depicted; however, various other modifications and alternate constructions can be made thereto without departing from the true spirit and scope of the invention.

DESCRIPTION OF THE PREFERRED EMBODIMENT

Figure 1:
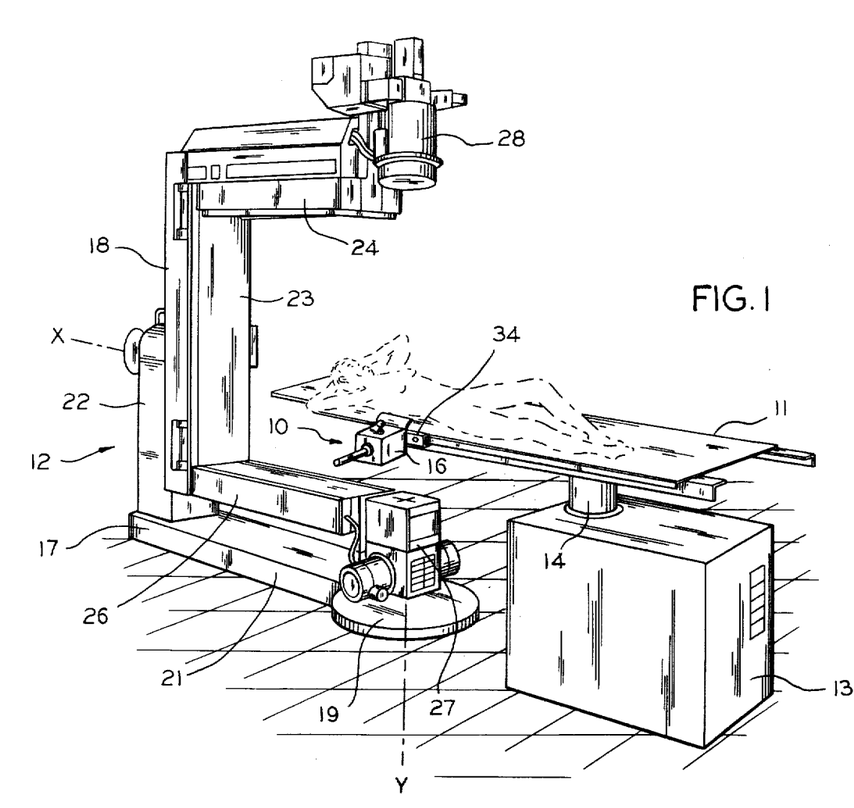
FIG. 1 is a perspective view of a cardiovascular table and associated "L/U-arm" assembly with the present invention embodied therein.

Referring now to FIG. 1, the invention is shown generally at 10 as installed on a cardiovascular table 11 in the close vicinity of an L/U-arm assembly, shown generally at 12. Representative of such a table and L/U-arm combination is one manufactured and sold commercially by XRE Corporation for use in hospital vascular procedure rooms. The present invention will be described in terms of its application to such an apparatus; however, it should be recognized that its concepts may be applicable and useful for controlling the motion of other types of multiple element mechanisms.

The table 11, which is supported by a support base 13 and an associated support post 14, is designed to remain in a horizontial disposition for supporting a patient to be examined. Means are provided to selectively position the table 11 by a proper operation of the control box 16 of the present invention 10. Such table movements which are possible include up and down movement, longitudinal movement, rotational movement, and transverse horizontal movement, any of which can be accomplished individually or in combination with another movement. The particular manner in which an operator brings about these individual movements will be more fully described hereinafter.

The L/U-arm assembly is so called because of its component parts, an L-element represented by the numeral 17 and a U-element designated by the numeral 18. A combination of these two elements provides a versatile support system for the movement of radiographic and fluoroscopic components to desired angles and positions relative to the patient being examined. The L-element 17 comprises serially connected hub 19, horizontal arm 21 and vertical arm 22. The hub 19 is rotatably mounted to the floor and has means connected thereto for rotating the L element 17 about the axis of the hub 19, as indicated at Y, in response to the control box 16. Rotation can be made to occur in either direction, and safety stops are provided to prevent rotational movement beyond the positions which may be detrimental to the integrity of the table 11. In order to facilitate this rotation, while at the same time supporting the L element horizontal arm 21 and its associated load, it may be desirable to have a wheel assembly of the caster type, or the like (not shown) under the free end of the horizontal arm 21. Disposed in the upper end of the L-element vertical arm 22 is a horizontally disposed shaft for support of the U-element in a manner which allows it to be rotated on the horizontal axis indicated by the letter X.

The U-element 18 comprises a middle arm 23 which is rotatably mounted at its midpoint to the L element vertical arm 22, and upper and lower horizontal arms 24 and 26, respectively. The lower arm 26 has an x-ray tube 27 and its associated components attached to the free end thereof, and the upper arm 24 has attached to its free end an image intensifier tube 28 and its associated equipment. The purpose of the L/U-arm support system is to provide a versatile support system for the oppositely disposed tube 27 and image intensifier tube 28 such that the combination can be selectively situated at desired positions and angles with respect to the body to be x-rayed. Accordingly, even though the U-arm element 18 is described in terms of upper and lower arms, it will be understood that the U-element can be rotated through a 200° range, and, as such, the "upper" arm 24 may, at times, actually be disposed below the "lower" arms 26.

It should be mentioned here that the present invention allows for both the L-element and the U-element to be rotated on their respective axes, and for the table 11 to be moved in one or two planes, all simultaneously.

Figure 2:
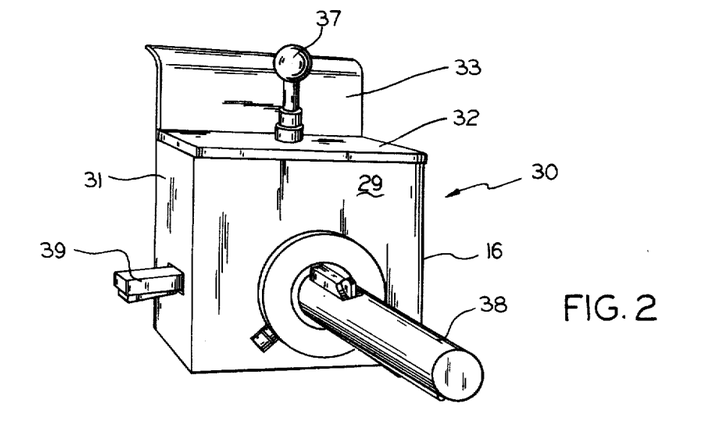
FIG. 2 is a perspective view of the control box portion thereof.

Positional control of each of the L and U-elements 17 and 18, respectively, as well as the table 11 is maintained by the control box 16, and any positional movements of those elements is initiated by an operator's selective modulation of the various handles and levers of the control box 16 as shown in FIG. 2. The control box 16 includes a front wall 29, a left sidewall 31, a right sidewall 30 and a top wall 32. A rear wall 33 is provided and includes an upward extending free portion which acts as a guard rail between the patient and the control box 16. There is attached to the back of the rear wall 33 a bracket 34 (see FIG. 1) which is slidably disposed on a tongue element of the table rail. A clamping screw 36 is provided on the bracket 34 to temporarily fix the position of the control box at a desired location on the table rail.

Control handles, which are available to the operator to modulate the control box 16, include a joystick 37 at the top of the box, an L/U-arm control handle 38 extending from the front of the box, and a table height control mechanism 39 extending from the left side of the box. Briefly, the joystick 37 is operable in three different directions to release the table lock for the longitudinal, transverse, or rotational movement, respectively. The L/U arm control handle 38 is operable to cause powered rotation of either or both of the L and U-elements, and also provides a separate function for releasing the table lock in both the longitudinal and transverse directions. The table height control mechanism 39 provides for the powered movement of the table in the upward or downward directions. Electrical communication from the joystick 37, L/U arm control handle 38, and the table height control mechanism 39 is provided to the various power and locking mechanisms by way of electrical wiring (not shown) which leads from the control box 16 by way of the right sidewall 30. A more detailed account of the operation of each of the control handles is provided hereinafter.

Figure 3:
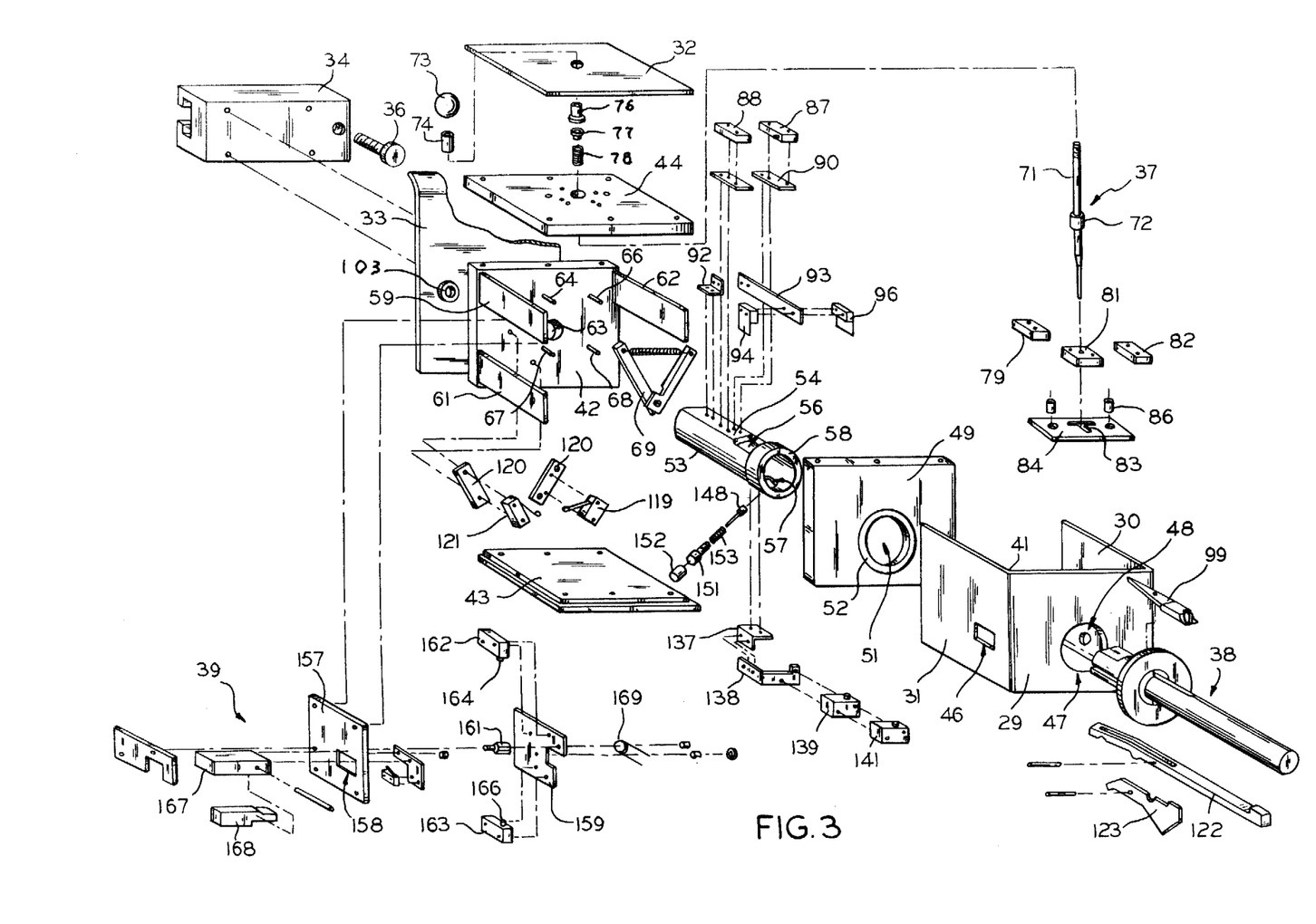
FIG. 3 is an exploded view of the control box.

Referring now to FIG. 3, the various parts of the control box 16 are shown in their relative exploded positions. A box housing is provided to include a U-shaped housing element 41, a back frame element 42, a bottom element 43, and a top element 44. The U-shaped housing element 41 comprises the integrally formed left sidewall 31, front wall 29, and right sidewall 30, with respective apertures 46, 47 and 48 formed therein for the passing through of the table height control mechanism 39, the L/U arm control handle 38, and the various wiring, respectively. A backing plate 49 is provided at the inner side of the front wall 29 for support purposes and includes a circular opening 51 and associated bearing 52. Projecting through the aperture 48 and the opening 51, and being rotatably supported by the bearing 52, is a cylinder 53 having a flattened top surface 54 for the mounting of switches in a manner to be more fully described hereinafter. Upper and lower openings 56 and 57, respectively, are provided in the cylinder 53 to permit mechanical interconnection from portions of the L/U arm control handle 38 which fit inside the cylinder 53, and switching mechanisms on the outer side of the cylinder 53. A collar 58 is disposed on the one end of the cylinder 53 which, when the cylinder is in the assembled position, abuts the outer face of the front wall 29, such that the collar 58 is outside the housing and the remaining portion of the cylinder is inside the housing. Associated with the collar 58 is a retainer pin assembly which operates to lock the L/U arm control handle 38 into its installed position as will be described more fully hereinafter in connection with FIGS. 4 and 5 hereof.

Returning now to further discussion of the housing assembly, the back frame element 42, which is rigidly secured to the rearwall 33 by threaded fasteners or the like (not shown), has upper and lower reinforcing bars 59 and 61, respectively, projecting forwardly on the left side and an upper reinforcing bar 62 projecting forwardly from the right side. These bars are connected to the back frame element 42 as by screws or the like. At the center of the backframe element 42 is an aperture 63 for rotatably and supportably receiving an axle extending from the rear solid-end portion of the cylinder 53. Upper left, upper right, lower left, and lower right stop posts, 64, 66, 67 and 68, respectively, extend from the backframe element 42 and serve to properly limit the rotational movement of a biasing mechanism 69 which is attached to and operates with the cylinder 53 in such a manner as to bias the L/U arm control handle 38 to the neutral position as will be more fully described hereinafter.

Before further discussion is given to the details of the system for controlling the L/U arm, it may be best to briefly describe the table lock joystick 37 and its associated mechanism. The elongate joystick shaft 71 is disposed with its lower end projecting down into holes formed in the central portions of the top wall 32 and top element 44, which are fastened together by screws or the like. A spherical bearing 72 fixes the axial position of the shaft 71 and allows it to be rotated within the top wall combination. The handle know 73 and shaft collar 74 are attached at the upper end of the joystick shaft 71 while a rubber bushing 76 fits over the upper end of the shaft 71 and projects upwardly through the central hole of the top wall 32. Also, disposed over the upper end of the shaft 71 is an aluminum insert 77 and a positioning spring 78 which is held in place by the insert 77. The spring 78 functions to bias the shaft 71 to a neutral position, that is to a position substantially normal to the top wall 32. The free or lower end of the shaft 71 then extends downwardly to engage the contact of any one of the three switches, represented by the numerals 79, 81 and 82, to effect a locking or an unlocking of the patient table position. Movement of the lower end of the shaft 71 is selectively restricted by a T-slot 83 in a plate 84 which is secured to the lower side of the top element 44 with a pair of spacers 86 disposed therebetween.

In operation, the joystick shaft 71 can be moved against the spring bias to any one of three positions to activate the associated switch in order to either engage (one movement) or release (two movements) the lock of the table in any one of the longitudinal, lateral, or rotational paths of movement. Operation of the joystick does not cause an application of power to the movement of the table, but rather a simple unlocking of the table to allow a manual movement of the table in the longitudinal, lateral or rotational directions.

Figures 4, 5:
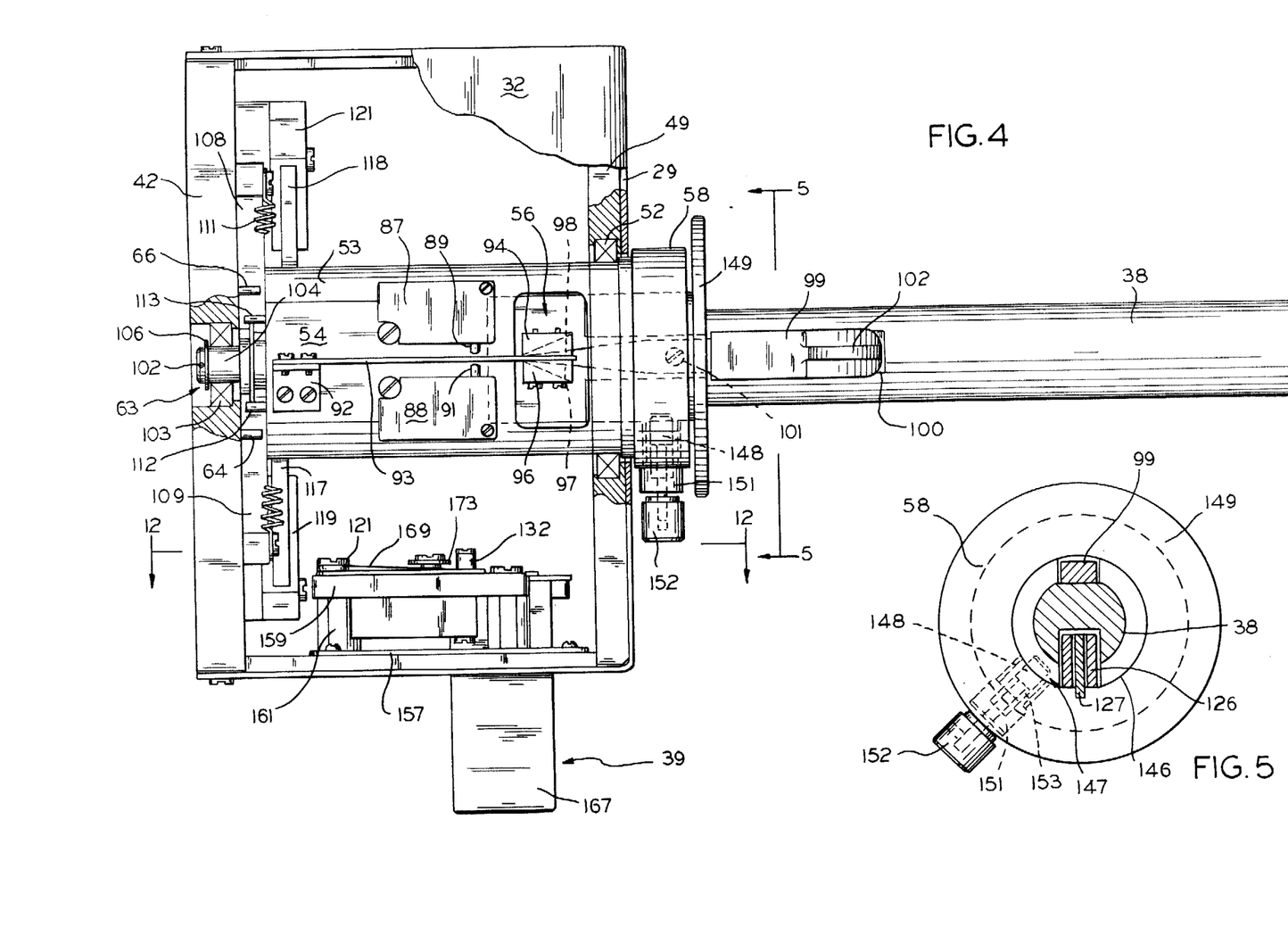
FIG. 4 is a top view thereof with portions being either broken away and/or sectioned to provide expanded visibility.
FIG. 5 is a transverse sectional view of the handle portion thereof as seen alone line 5—5 of FIG. 4.
Figure 6:
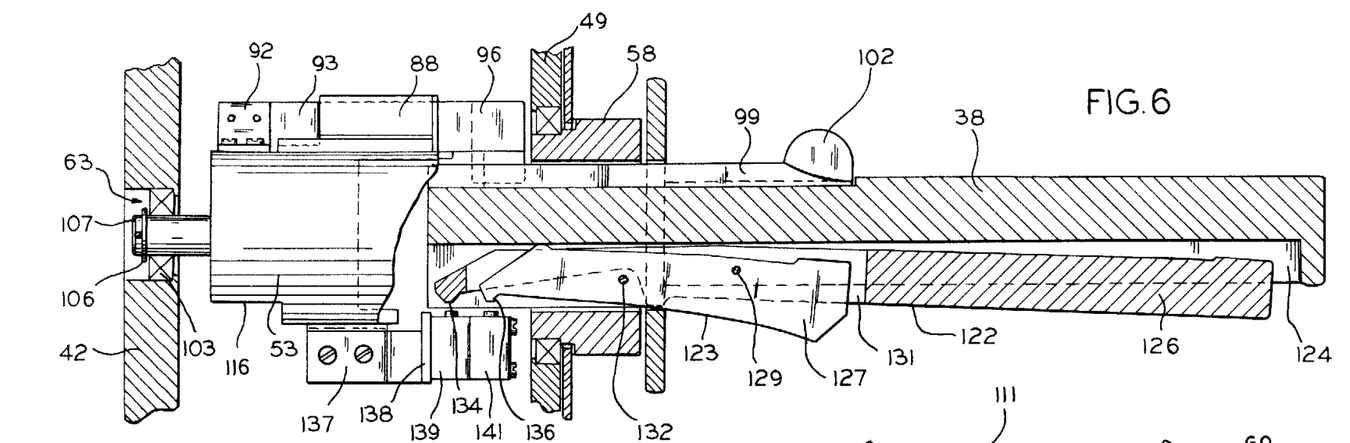
FIG. 6 is a longitudinal sectional view of the handle portion and the associated control box interfacing portions thereof.

Returning now to further discussion of the L/U arm control handle 38 and its associated functions, the removable handle is shown in its installed position in FIGS. 4 and 6. First, discussion will be given to those mechanisms involved in the positional control of the L-support element, and for that purpose, reference will be made to FIGS. 4, 6 and 8 as well as to FIG. 3. Symmetrically mounted by pads 90, in side-by-side relationship on the flat serface 54 of the cylinder 53, is a pair of switches 87 and 88 having respective contacts 89 and 91 oppositely projecting toward the center, with a small gap therebetween. Also attached to the flat surface 54, by way of a bracket 92, is a longitudinally extending leaf spring 93 which passes through the gap between the contacts 89 and 91 and terminates in the vicinity of the upper opening 56 of the cylinder 53. Attached to the free end of the leaf spring 93 and extending downwardly into the upper opening 56 is a pair of transfer blocks 94 and 96 interconnected by screws, or the like, with one block on each side of the spring 93. Formed in the front edge of the blocks, at the lower portions thereof, is a wedge shaped opening 97 as shown by dotted lines in FIG. 4, for receiving a pointed end 98 of an L-arm control lever 99 which is rotatably mounted on the flat surface 100 of the L/U-arm control handle 38. As will be seen in FIG. 8, the control lever 99 is rotatable within the flat surface slot 100 to allow a movement of the pointed end 98. As the pointed end 98 moves from its central position, it engages one of the transfer blocks 94 or 96 which will in turn, if the force is sufficient, overcome the bias of the leaf sring 93 and allow one of the switch contacts 89 or 91 to be depressed. Thus, rotation of the lever 99 in a clockwise direction will cause the switch contact 89 to be depressed, which will in turn cause a rotation of the L-arm in a clockwise direction. Similarly, rotation of the lever 99 in a counterclockwise direction will cause a rotation of the L-arm in the counterclockwise direction. For safety reasons, the degree of powered movement of the L-arm is restricted to plus or minus 95 degrees from the central position shown in FIG. 1.

Figure 8:
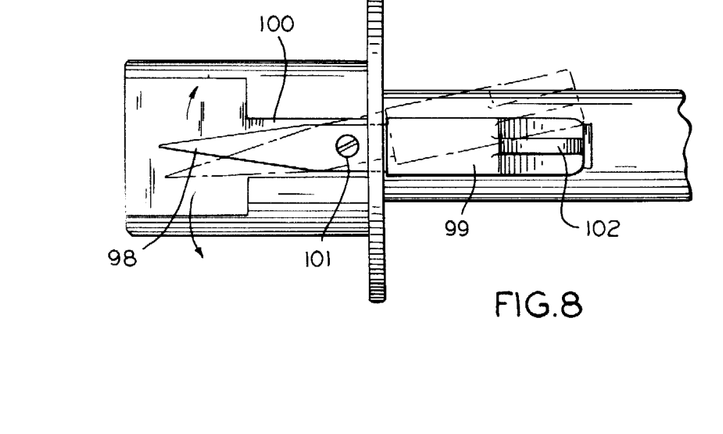
FIG. 8 is a partial top view of the control handle with an included control lever.
Figure 9:
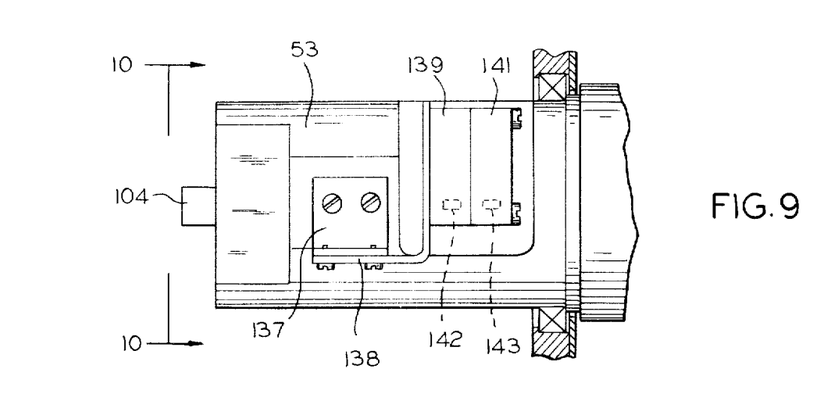
FIG. 9 is a bottom view of portions of the control box internal components.
Figure 10:
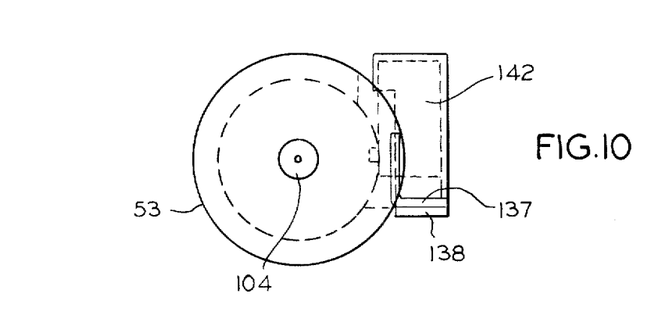
FIG. 10 is a rear view of portions thereof.

It should be recognized that the leaf spring 93 acts as both a means for transferring the lever action force to the switch contacts and for biasing the lever 99 to a neutral position. Its biasing function is a convenience and safety feature which automatically returns the lever 99 to the neutral position whenever an operator ceases to apply pressure to the lever 99. Efficient and easy thumb control of the lever 99 is facilitated by an upperwardly extending flange 102 at its one end thereof.

Changing now to a discussion of the manner in which the U-arm support element is rotatably positioned by the use of the L/U-arm control handle 38, reference will be made primarily to FIGS. 3, 4 and 7. As will be seen in FIG. 4, the cylinder 53 is rotatably mounted within the housing by way of the bearing 52 at its one end, and at its other end by a bearing 103 which is disposed in the aperature 63. The axle 104 which projects from the rear solid end of the cylinder 53 is thus rotatably disposed in the bearing 103 and is held in place by a washer 106 and a threaded fastener 107. Also disposed on the axle 104 is the biasing mechanism 69 which comprises a pair of biasing arms 108 and 109 with a coil spring 111 interconnecting their free ends. Movement of the biasing arms 108 and 109 is controlled and/or restricted by the stop posts 64, 66, 67 and 68 extending from the back frame element 42 and by the engagement posts 112 and 113 extending from the rear face 114 of the cylinder 53. As will be seen in FIGS. 6 and 7, the cylinder 53 has a lower flat surface 116 which, when rotated on the axle 104, will cause engagement with one of the spring contacts 117 or 118 of electrical switches 119 or 121, respectively. Activation of one of these switches in turn causes power to be applied to an electric motor for rotating the U-arm in a particular direction. Rotation of the cylinder 53 in the opposite direction will then cause a disengagement with that spring contact and will result in a turning off of the power to the rotational motor. Further rotation of the cylinder 53 in the opposite direction will cause engagement with the other spring contact and will result in a rotation of the U-arm in the opposite direction until the U-arm reaches the maximum safe position or until the cylinder is again reversed to disengage from the spring contact. In operation, rotation of the L/U arm control handle 38, and thus the cylinder 53, in the clockwise direction results in a clockwise rotation of the U-arm, and counterclockwise rotation of the handle results in a counterclockwise rotation of the U-arm.

Figure 7:
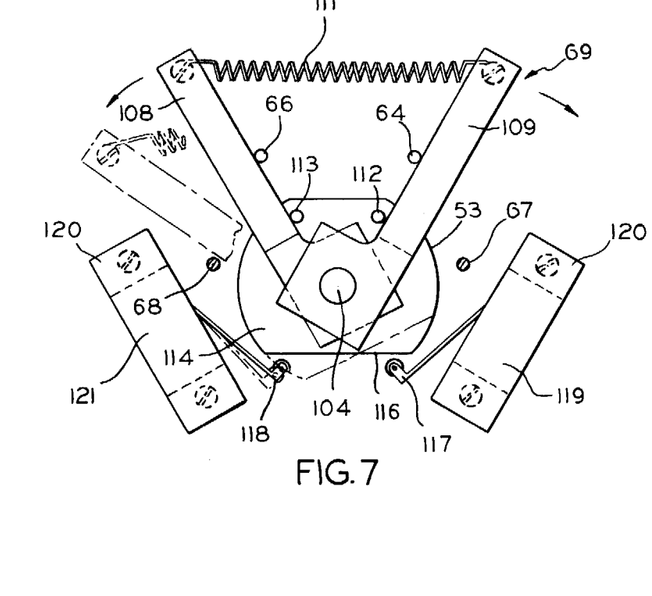
FIG. 7 is a rear view of the biasing mechanism within the control box.

Referring now back to FIG. 7, the manner by which the biasing mechanism 69 and the associated stop and engagement posts control the rotation of the cylinder 53 will be described. First, it will be seen that the biasing arms 108 and 109 are biased against the stop posts 66 and 64 respectively, extending from the back frame element 42 by operation of the coil spring 111. This is the neutral position as shown by solid lines in FIG. 7. It will be recognized that because of the contact of the biasing arms 108 and 109 with the engagement pins 113 and 112 extending from the cylinder rear face, the cylinder 53 and the L/Uarm control handle 38 will also be biased to the neutral position. Considering now a rotation of the L/U arm control handle 38 in the clockwise direction, the cylinder 53 will rotate in a clockwise direction and engage the spring contact 18 which in turn will activate the switch 121 and cause the U-arm to rotate in the clockwise direction. As the cylinder 53 is rotated, the engagement pin 113 causes a rotation of the biasing arm 108 until it comes to rest against the stop post 68 as shown by the dotted line position of FIG. 7. In this position, the U-arm will continue to rotate in a clockwise direction until it reaches the maximum safe limit which may typically be a position of 100° from the central position as shown in FIG. 1. When the operator releases the rotational pressure on the control handle 38, the coil spring 111 will cause the biasing arm 108 to return to its initial position and in doing so the biasing arm 108 will by way of direct contact with the engagement pin 113, will cause the cylinder 53 and the associated control handle 38 to return to their neutral positions. Rotation of the U-arm in the counterclockwise direction is controlled in a similar manner.

Figure 11:
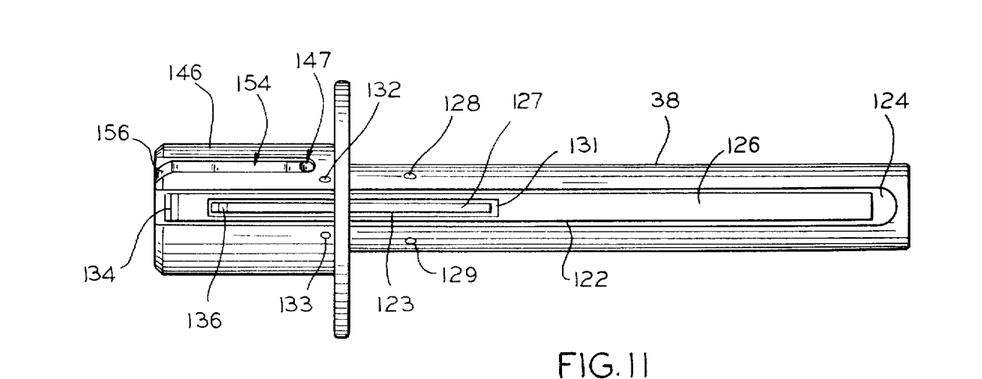
FIG. 11 is a bottom view of the control handle and associated levers.

Also included as part of the L/U-arm control handle 38 are the enabling lever 122 and panning lever 123, both shown in FIGS. 6 and 11. A longitudinally extending slot 124 is formed in the lower side of the L/U-arm control handle 38 for pivotally retaining these levers in such a manner as to provide outter ends 126 and 127, respectively, which are easily accessible for the operator to individually depress with the same hand which is used to rotate the handle 38 and the lever 99. As will be seen, the enabling lever 122 is rotatably mounted within the handle slot 124 by the use of a pin 128 mounted in the hole 129. Likewise, the panning lever 123 is mounted within a slot 131 in the enabling lever by a pin 132 disposed in the holes 133. A pivoting of the enabling lever 122 and the panning lever 123 about their respective pivot points thus causes a downward movement of their respective contact ends 134 and 136 within the cylinder 53 to activate switches for bringing about the respective enabling and panning-unlock functions.

Mounted to the underside of the cylinder 53, by a pair of L-shaped brackets 137 and 138, are a pair of switches 139 and 141 which extend up into the lower opening 57 of the cylinder 53 in such a manner that their respective plungers 142 and 143 are engagable by the respective contact points 134 and 136. A depression of the enabling lever 122 by the operator thus causes activation of the switch 139 which in turn activates the respective electric circuits which allow the individual L and U-arm rotation systems to be operational. Thus, unless the enabling lever 122 is depressed, any rotation of the handle 38 or the lever 99 will cause no movement of the individual L or U-arms. If either the control handle 38 or the lever 99 is first rotated and then the enabling lever 122 is depressed, the respective L or U-arm element will be caused to rotate in the direction of rotation of the handle 38 or the lever 99.

In a similar manner, depression of the panning lever 123 by the operator will cause an activation of the switch 141 which in turn will operate to disengage two of the three locking mechanisms within the position control of the table 11 to allow the table 11 to be moved in the longitudinal and/or transverse directions. The effect of this panning lever is then to override the table lock joystick 37 for two of its three positions.

In view of the above discussion relating to the operation of the L/U-arm control handle 38, with its associated L-arm control lever 99, enabling lever 122, and panning lever 123, it will be seen that an operator can, with the use of a single hand, grasp the handle 38 and, either simultaneously or individually, rotate the handle 38, rotate the lever 99, depress the enable lever 122, and/or depress the panning lever 123 to cause a simultaneous or individual movement of the L-arm element 17, the U arm element 18 and/or the table 11. In addition to providing for the control of all of these functions with a single handle, this invention includes features which allow that single handle to be selectively removed from the control box for purposes of sterilization as by autoclaving or the like.

As discussed hereinabove, the L/U arm control handle 38 is adapted to be disposed with its one end inside the one end of the cylinder 53 in such a way that the L-arm control lever 99 extends to the vicinity of the opening 56 and the enabling lever 122 and the panning lever 123 extend to the vicinity of the cylinder lower opening 57. When in the installed position, a shoulder 149 on the control handle 38 is in close disposition with one face of the cylinder collar 58. Retention of the control handle 38 within the cylinder 53 is maintained by way of the retaining system shown in FIGS. 3, 4 and 5. As will be seen, the inner shank 146 of the control handle 38 has a recess 147 formed therein for the receiving of a pin 148 of the retention mechanism. The pin 148 is slidably disposed within a journal 151 which in turn passes through the collar 58 with its axis perpendicular to the collar 58. A knob 152 is disposed on the one end of the pin 148 and a biasing spring 153 acts to bias the pin 148 to the inward, engaged position. A pulling out of the knob 152 will cause disengagement of the pin 148 from the recess 147 and allow the control handlle 38 to be removed from the cylinder 53. In order to facilitate the return of the handle 38 to its installed position, a groove 154 and associated inclined surface 156 is provided in the handle inner shank 146 to allow the pin 148 to easily ride into the recess 147 by a simple pushing of the handle 138 inwardly. This structure can be seen in FIG. 11.

Figure 12:
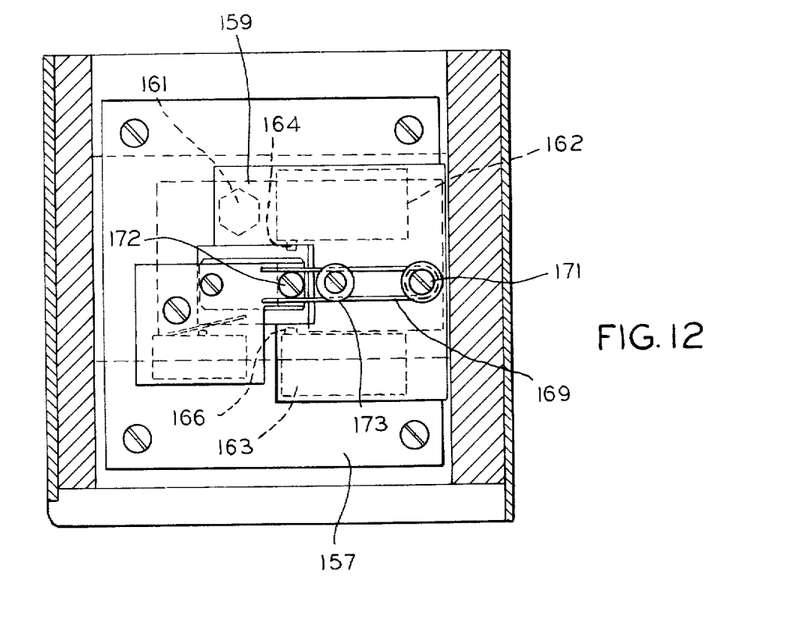
FIG. 12 is a sectional view of the control box as seen along lines 12—12 of FIG. 4.
Figure 13:
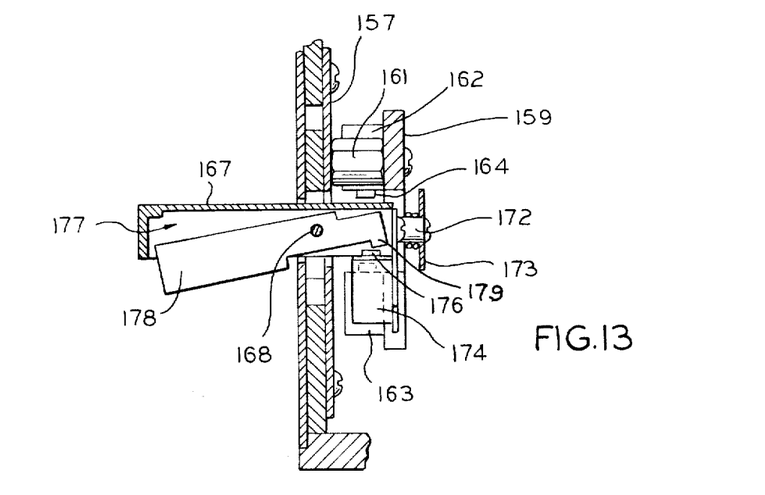
FIG. 13 is a partial sectional view of the table height control portion of the control box.

Turning now to the table height control mechanism shown generally at 39, reference will be made to FIGS. 3, 12 and 13. A base plate 157 is mounted on the inner sides of the reinforcement bars 59 and 61, the base plate 157 having a rectangular hole 158 which is aligned with the aperture 46 of the housing element 41. A mounting plate 159 is then secured to the base plate 157 with spacers 161 to provide a cavity therebetween. Mounted on the inner side of the mounting plate 159, in the cavity provided, are the table height down and up switches 162 and 163 having plungers 164 and 166, respectively. Operation of the down and up switches 162 and 163 is accommodated by the table height lever 167 which extends through the aperture 46 and the hole 158 with its inner end extending to the vicinity of the switch plungers 164 and 166. The table height lever 167 is pivotally mounted by a pin 168 such that when its outer end is pushed downwardly by the operator, the plunger 164 is depressed and the down switch 162 is activated to cause a powered movement of the table in the downward direction. Similarly, if the table height lever 167 is pushed upwardly at its outer end, its inner end causes a depression of the plunger 166 and an activation of the up switch 163 to cause the table to move upwardly. A biasing of the table height 167 to a neutral position is provided by a spring 169 which is attached to the mounting plate 159 by a screw 171 in such a way that its free ends are engagable by an extension 172 on the inner end of the table height lever 167. A washer 173 is provided to retain the spring 169 in close alignment with the face of the mounting plate 159.

An enabling mechanism is provided for the table height control in order to prevent inadvertent or accidental operation. Mounted to the inner end of the table height lever 167 is an enabling switch 174 having an activation plunger 176. As will be seen in FIG. 13, the table height lever 167 has a cavity 177 formed therein to pivotally receive enabling lever 178 therein, with the enabling lever mounted on the common pin 168 with the table height lever 167. The inner end 179 of the enabling lever 178 is so disposed with respect to the activation plunger 176 that the enabling switch 174 will allow the electrical enablement of the up and down power system for the table 11 to be operable only when the enabling lever 178 is lifted by the operator. Movement of the table in the upward or downward position is thus accomplished by the operator's first lifting up on the enabling lever 178 and then by moving the table height lever 167 in either the upward or downward position.

Though the invention has been described in particular detail, it will be understood by those familiar with the art that various other structures can be used to obtain the results contemplated by the present invention.

We claim:

1. An improved position control system for a medical diagnostic imaging apparatus of the type having an L-shaped support element rotatably disposed on a vertical axis, a U-shaped support element rotatably supported on a horizontal axis at the upper end of the L-shaped support element, and individual rotation systems for independently rotating the respective support elements on their axes, wherein the improvement comprises:
   a control box which houses portions of the individual rotation systems, said box having an aperture formed therein;
   a control handle for extending into said aperture to form a mechanical connection to the individual rotation systems; and
   means for operating said control handle with a single hand of an operator to selectively actuate at least one of said rotation systems.

2. An improved position control system as set forth in claim 1 wherein said control handle has rotatably attached thereto an enabling lever, said enabling lever having its one end engagable with an enabling apparatus for enabling said operating means only when the other end of said enabling lever is moved on said handle by an operator.

3. An improved position control system as set forth in claim 1 wherein the imaging aparatus includes a patient table and further wherein said control handle has rotatably attached thereto a panning lever, said panning lever having its one end engagable with a table panning mechanism for unlocking said table for movement in at least one plane when the other end of said panning lever is moved on said handle by an operator.

4. An improved position control system as set forth in claim 1 and including means for temporarily removing said control handle from said control box aperture for purposes of sterilization.

5. An improved position control system as set forth in claim 4 wherein said control handle removal means comprises a pin so biased as to engage a hole in said control handle.

6. An improved position control system as set forth in claim 4 wherein said control handle removal means further includes an inclined surface on said control handle for frictional engagement with said pin to facilitate the replacement of said handle to said control box aperture.

7. An improved position control system as set forth in claim 1 wherein said control handle is rotatable on the same axis as said control box aperture to actuate one of said rotation systems.

8. An improved position control system as set forth in claim 7 wherein said one of said rotation systems causes rotation of the U-shaped support element.

9. An improved position control system as set forth in claim 7 wherein the direction of rotation of said control handle corresponds to the direction of rotation of the support element which it causes to rotate.

10. An improved position control system as set forth in claim 9 and including means for biasing said control handle to a neutral position.

11. An improved position control system as set forth in claim 1 wherein said control handle has attached thereto a lever which is rotatable on said handle to activate one of said actuation systems.

12. An improved position control system as set forth in claim 11 wherein the direction of rotation of said lever corresponds to the direction of rotation of the support element which it causes to rotate.

13. An improved position control system as set forth in claim 11 wherein said one of said rotation systems causes rotation of the L-shaped support element.

14. An improved position control system as set forth in claim 11 wherein the juxtaposition of said lever and said handle on which it is mounted are such as to facilitate the simultaneous rotation of both by a single hand of an operator.

15. An improved position control system as set forth in claim 11 wherein said handle is rotatable on its axis and said lever is rotatable on an axis perpendicular to the axis of said handle.

16. In a medical diagnostic imaging apparatus comprising an L-shaped support structure rotatably mounted on a vertical axis and having a U-shaped support structure mounted on a horizontal axis of the L-shaped support structure, a control assembly for causing selective rotation of the respective support structures, comprising:
   a control housing adapted to be mounted in a position accessible to an operator, said control housing having means for individually communicating with each of said support structures;
   a handle being rotatably mounted on and extending from said control housing, said handle having inner and outer ends with said inner end being mechanically linked to said communicating means for causing a rotation of one of said support structures when said handle outer end is rotated;
   and a lever rotatably mounted on said handle, said lever having inner and outer ends with said inner end being linked to said communication means for causing a rotation of the other of said support structures when said lever outer end is rotated on said handle, said handle and said lever being so juxtapositioned as to facilitate the simultaneous rotation of both by a single hand of an operator.

17. A control assembly as set forth in claim 16 wherein said U-shaped support structure is caused to rotate by rotation of said handle.

18. A control assembly as set forth in claim 16 wherein said L-shaped support structure is caused to rotate by rotation of said lever.

19. A control assembly as set forth in claim 16 wherein said means for communicating includes electrical switches separately activated by the respective rotations of said handle and said lever.

20. A control assembly as set forth in claim 16 wherein said means for communicating includes a pair of electric motors for rotating the respective support structures in response to the rotation of the respective handle and lever.

21. A control assembly as set forth in claim 16 wherein the direction of rotation of said lever corresponds to the direction of rotation of the other of said support structures.

22. A control assembly as set forth in claim 16 wherein said lever is mounted so as to be rotatable on an axis which is perpendicular to the axis of said handle.

23. A control assembly as set forth in claim 16 and including an enabling lever rotatably attached to said handle, said enabling lever having inner and outer portions, said inner portion extending into the housing to enable the rotation of said pair of support structures only when the outer portion of said enabling lever is rotated on said handle.

24. A control assembly as set forth in claim 16 wherein said housing is mounted on a patient table which is movable in at least one plane and wherein said housing includes an actuation means for so moving said patient table and further wherein said shaft has rotatably attached thereto a panning lever having an inner and an outer portion, said lever innerportion extending into said housing and being operable with said actuating means for moving said patient table when said panning lever outer portion is rotated on said handle.

25. A control assembly as set forth in claim 16 wherein the direction of rotation of said handle corresponds to the direction of rotation of one of said support structures.

26. A control assembly as set forth in claim 25 and including means for biasing said handle to a neutral position.

27. A control assembly as set forth in claim 16 and including means for retaining said handle within said housing, said retaining means having means for temporarily disconnecting and removing said handle for purposes of sterilization.

28. A control assembly as set forth in claim 27 wherein said disconnecting means includes an inclined surface on said handle for facilitating a reconnection of said handle with said control housing.

29. A position control system for a medical diagnostic imaging apparatus having an L-shaped support element rotatably disposed on a vertical axis, a U-shaped support element rotatably supported on a horizontal axis at the upper end of the L-shaped support element, individual rotation systems for independently rotating the respective U and L-shaped support elements on their axes, and a table for positioning a patient in the vicinity of the support elements, comprising:

a control box which houses portions of the individual rotation systems, said box having an aperture formed therein;

a control handle for extending into said aperture to form a mechanical connection to the individual rotation systems, said control handle comprising a shaft which is rotatable on the same axis as that of said control box aperture to actuate one of said rotation systems for rotating the U-shaped support element in a direction corresponding to the direction of rotation of said shaft;

means for temporarily removing said control handle for purposes of sterlization and for replacing said control handle in the control box aperature;

an L-arm lever attached to and rotatable on said shaft to actuate another of said rotation systems to rotate said L-shaped support element in a direction corresponding to the direction of rotation of said L-arm lever;

an enabling lever rotatably attached to said shaft, said enabling lever having its one end engagable with an enabling apparatus within said control box for enabling said rotation systems only when the other end of said enabling lever is moved on the shaft by an operator; and a panning lever attached to said shaft, said panning lever having one end engagable with a table panning mechanism for unlocking said table for movement in at least one plane when the other end of said panning lever is moved on said shaft by an operator; said shaft, L-arm lever, enabling lever, and panning lever all being so positioned as to be simultaneously operated by a single hand of an operator.

* * * * *